United States Patent
Gannoe et al.

(10) Patent No.: US 7,214,233 B2
(45) Date of Patent: *May 8, 2007

(54) METHODS AND DEVICES FOR MAINTAINING A SPACE OCCUPYING DEVICE IN A RELATIVELY FIXED LOCATION WITHIN A STOMACH

(75) Inventors: James Gannoe, Palo Alto, CA (US); Craig Gerbi, Mountain View, CA (US)

(73) Assignee: Satiety, Inc., Palo Alto, CA (US)

( * ) Notice: Subject to any disclaimer, the term of this patent is extended or adjusted under 35 U.S.C. 154(b) by 595 days.

This patent is subject to a terminal disclaimer.

(21) Appl. No.: 10/366,818

(22) Filed: Feb. 13, 2003

(65) Prior Publication Data

US 2004/0044354 A1 Mar. 4, 2004

Related U.S. Application Data

(63) Continuation-in-part of application No. 10/232,505, filed on Aug. 30, 2002, now Pat. No. 6,981,978.

(51) Int. Cl.
*A61B 17/08* (2006.01)
*A61B 19/00* (2006.01)
*A61M 29/00* (2006.01)

(52) U.S. Cl. .................. 606/153; 128/898; 606/192

(58) Field of Classification Search ............... 606/153, 606/192, 195, 197; 128/898, 899; 600/207; 623/23.64, 23.67; 604/891.1; 607/133
See application file for complete search history.

(56) References Cited

U.S. PATENT DOCUMENTS 2,108,206 A 2/1938 Meeker 2,508,690 A 5/1950 Schmerl (Continued)

FOREIGN PATENT DOCUMENTS

EP 0 137 878 A1 4/1985

(Continued)

OTHER PUBLICATIONS

T. M. Boyle et al., "Small Intestinal Obstruction Secondary to Obturation by a Garren Gastric Bubble", *The Am. J. of Gastroenterology*, vol. 82, No. 1, 1987, pp. 51-53.

(Continued)

*Primary Examiner*—Julian W. Woo
(74) *Attorney, Agent, or Firm*—Fulwider Patton LLP

(57) ABSTRACT

Methods and devices for maintaining a space-occupying device in a fixed relationship relative to a patient's stomach by manipulation of the stomach. In one variation, two or more regions of the stomach wall are brought into approximation with one another and secured together in a manner that secures a space-occupying device within the stomach of the patient. In another variation, two or more regions of the stomach wall are wrapped around a space-occupying device to maintain the position of the space-occupying device relative to the stomach wall. In another variation, a system having a space-occupying member and a locking member capable holding the space-occupying member against the inner wall of the stomach are provided. In a further variation, a pouch is created within the stomach that receives and retains a space-occupying device.

18 Claims, 7 Drawing Sheets

U.S. PATENT DOCUMENTS

| | | |
|---|---|---|
| 3,395,710 A | 8/1968 | Stratton et al. |
| 3,986,493 A | 10/1976 | Hendren, III |
| 4,057,065 A | 11/1977 | Thow |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,315,509 A | 2/1982 | Smit |
| 4,402,445 A | 9/1983 | Green |
| 4,416,267 A | 11/1983 | Garren et al. |
| 4,434,066 A | 2/1984 | Lewis |
| 4,458,681 A | 7/1984 | Hopkins |
| 4,485,805 A | 12/1984 | Foster, Jr. |
| 4,501,264 A * | 2/1985 | Rockey ..................... 128/898 |
| 4,547,192 A | 10/1985 | Brodsky et al. |
| 4,558,699 A | 12/1985 | Bashour |
| 4,592,339 A * | 6/1986 | Kuzmak et al. ............. 128/899 |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,641,653 A | 2/1987 | Rockey |
| 4,646,722 A | 3/1987 | Silverstein et al. |
| 4,648,383 A | 3/1987 | Angelchik |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A * | 5/1990 | Garay et al. ............. 604/891.1 |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,408 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |

| | | | | | | |
|---|---|---|---|---|---|---|
| 5,879,371 | A | 3/1999 | Gardiner et al. | 6,558,400 B2 | 5/2003 | Deem et al. |
| 5,887,594 | A | 3/1999 | LoCicero, III | 6,561,696 B1 | 5/2003 | Rusnak et al. |
| 5,888,196 | A | 3/1999 | Bonutti | 6,561,969 B2 | 5/2003 | Frazier et al. |
| 5,897,534 | A | 4/1999 | Heim et al. | 6,572,629 B2 | 6/2003 | Kalloo et al. |
| 5,897,562 | A | 4/1999 | Bolanos et al. | 6,592,596 B1 | 7/2003 | Geitz |
| 5,906,625 | A | 5/1999 | Bito et al. | 6,626,899 B2 | 9/2003 | Houser et al. |
| 5,910,105 | A | 6/1999 | Swain et al. | 6,632,227 B2 | 10/2003 | Adams |
| 5,910,149 | A | 6/1999 | Kuzmak | 6,663,598 B1 | 12/2003 | Carrillo, Jr. et al. |
| 5,921,993 | A | 7/1999 | Yoon | 6,663,639 B1 | 12/2003 | Laufer et al. |
| 5,927,284 | A | 7/1999 | Borst et al. | 6,663,640 B2 | 12/2003 | Kortenbach |
| 5,928,264 | A | 7/1999 | Sugarbaker et al. | 6,675,809 B2 | 1/2004 | Stack et al. |
| 5,935,107 | A | 8/1999 | Taylor et al. | 6,682,520 B2 | 1/2004 | Ingenito |
| 5,938,669 | A | 8/1999 | Klaiber et al. | 6,689,062 B1 | 2/2004 | Mesallum |
| 5,947,983 | A | 9/1999 | Solar et al. | 6,692,485 B1 | 2/2004 | Brock et al. |
| 5,964,782 | A | 10/1999 | Lafontaine et al. | 6,716,222 B2 | 4/2004 | McAlister et al. |
| 5,972,001 | A | 10/1999 | Yoon | 6,733,512 B2 | 5/2004 | McGhan |
| 5,972,002 | A | 10/1999 | Bark et al. | 6,736,822 B2 | 5/2004 | McClellan et al. |
| 5,976,161 | A | 11/1999 | Kirsch et al. | 6,740,098 B2 | 5/2004 | Abrams et al. |
| 5,980,537 | A | 11/1999 | Ouchi | 6,740,121 B2 | 5/2004 | Geitz |
| 5,993,464 | A | 11/1999 | Knodel | 6,746,489 B2 | 6/2004 | Dua et al. |
| 5,993,473 | A | 11/1999 | Chan et al. | 6,754,536 B2 | 6/2004 | Swoyer et al. |
| 6,015,378 | A | 1/2000 | Borst et al. | 6,755,849 B1 | 6/2004 | Gowda et al. |
| 6,030,364 | A | 2/2000 | Durgin et al. | 6,755,869 B2 | 6/2004 | Geitz |
| 6,030,392 | A | 2/2000 | Dakov | 6,756,364 B2 | 6/2004 | Barbier et al. |
| 6,042,538 | A | 3/2000 | Puskas | 6,764,518 B2 | 7/2004 | Godin |
| 6,044,847 | A | 4/2000 | Carter et al. | 6,773,440 B2 | 8/2004 | Gannoe et al. |
| 6,067,991 | A | 5/2000 | Forsell | 6,773,441 B1 | 8/2004 | Laufer |
| 6,074,343 | A | 6/2000 | Nathanson et al. | 6,786,898 B2 | 9/2004 | Guenst |
| 6,083,241 | A | 7/2000 | Longo et al. | 6,790,214 B2 | 9/2004 | Kraemer et al. |
| 6,086,600 | A | 7/2000 | Kortenbach | 6,802,868 B2 | 10/2004 | Silverman et al. |
| 6,113,609 | A | 9/2000 | Adams | 6,821,285 B2 | 11/2004 | Laufer et al. |
| 6,119,913 | A | 9/2000 | Adams et al. | 6,835,199 B2 | 12/2004 | McGuckin, Jr. et al. |
| 6,120,513 | A | 9/2000 | Bailey et al. | 6,835,200 B2 | 12/2004 | Laufer et al. |
| 6,136,006 | A | 10/2000 | Johnson et al. | 6,837,848 B2 | 1/2005 | Bonner et al. |
| 6,159,146 | A | 12/2000 | El Gazayerli | 6,840,423 B2 | 1/2005 | Adams et al. |
| 6,159,195 | A | 12/2000 | Ha et al. | 6,845,776 B2 | 1/2005 | Stack et al. |
| 6,165,183 | A | 12/2000 | Kuehn et al. | 6,896,682 B1 | 5/2005 | McClellan et al. |
| 6,179,022 | B1 | 1/2001 | Schneider et al. | 6,926,722 B2 | 8/2005 | Geitz |
| 6,179,195 | B1 | 1/2001 | Adams et al. | 6,966,919 B2 | 11/2005 | Sixto, Jr. et al. |
| 6,186,942 | B1 | 2/2001 | Sullivan et al. | 6,981,978 B2 * | 1/2006 | Gannoe ............... 606/153 |
| 6,186,985 | B1 | 2/2001 | Snow | 6,991,643 B2 | 1/2006 | Saadat |
| 6,197,022 | B1 | 3/2001 | Baker | 7,020,531 B1 * | 3/2006 | Colliou et al. ........... 607/133 |
| 6,200,318 | B1 | 3/2001 | Har-Shai et al. | 7,025,791 B2 | 4/2006 | Levine et al. |
| 6,206,822 | B1 | 3/2001 | Foley et al. | 7,033,378 B2 | 4/2006 | Smith et al. |
| 6,206,893 | B1 | 3/2001 | Klein et al. | 7,037,343 B2 | 5/2006 | Imran |
| 6,224,614 | B1 | 5/2001 | Yoon | 7,037,344 B2 | 5/2006 | Kagan et al. |
| 6,231,561 | B1 | 5/2001 | Frazier et al. | 7,063,715 B2 | 6/2006 | Onuki et al. |
| 6,248,058 | B1 | 6/2001 | Silverman et al. | 7,083,630 B2 | 8/2006 | DeVries et al. |
| 6,254,642 | B1 | 7/2001 | Taylor | 7,087,011 B2 | 8/2006 | Cabiri et al. |
| 6,273,897 | B1 | 8/2001 | Dalessandro et al. | 2001/0014800 A1 | 8/2001 | Frazier et al. |
| 6,279,809 | B1 | 8/2001 | Nicolo | 2001/0020190 A1 | 9/2001 | Taylor |
| 6,290,674 | B1 | 9/2001 | Roue et al. | 2001/0037127 A1 | 11/2001 | De Hoyos Garza |
| 6,302,917 | B1 | 10/2001 | Dua et al. | 2002/0035361 A1 | 3/2002 | Houser et al. |
| 6,312,437 | B1 | 11/2001 | Kortenbach | 2002/0040226 A1 | 4/2002 | Laufer et al. |
| 6,328,689 | B1 | 12/2001 | Gonzalez et al. | 2002/0047036 A1 | 4/2002 | Sullivan et al. |
| 6,338,345 | B1 | 1/2002 | Johnson et al. | 2002/0058967 A1 | 5/2002 | Jervis |
| 6,358,197 | B1 | 3/2002 | Silverman et al. | 2002/0072761 A1 | 6/2002 | Abrams et al. |
| 6,379,366 | B1 | 4/2002 | Fleischman et al. | 2002/0077661 A1 | 6/2002 | Saadat |
| 6,387,104 | B1 | 5/2002 | Pugsley, Jr. et al. | 2002/0078967 A1 | 6/2002 | Sixto, Jr. et al. |
| 6,398,795 | B1 | 6/2002 | McAlister et al. | 2002/0082621 A1 | 6/2002 | Schurr et al. |
| 6,416,535 | B1 | 7/2002 | Lazarus | 2002/0143346 A1 | 10/2002 | McGuckin, Jr. et al. |
| 6,423,087 | B1 | 7/2002 | Sawada | 2002/0165589 A1 | 11/2002 | Imran et al. |
| 6,432,040 | B1 | 8/2002 | Meah | 2002/0183768 A1 | 12/2002 | Deem et al. |
| 6,447,533 | B1 | 9/2002 | Adams | 2002/0193816 A1 | 12/2002 | Laufer et al. |
| 6,460,543 | B1 | 10/2002 | Forsell | 2003/0065340 A1 | 4/2003 | Geitz |
| 6,475,136 | B1 | 11/2002 | Forsell | 2003/0065359 A1 | 4/2003 | Weller et al. |
| 6,491,707 | B2 | 12/2002 | Makower et al. | 2003/0093117 A1 | 5/2003 | Saadat |
| 6,494,888 | B1 | 12/2002 | Laufer et al. | 2003/0109892 A1 | 6/2003 | Deem et al. |
| 6,506,196 | B1 | 1/2003 | Laufer | 2003/0109931 A1 | 6/2003 | Geitz |
| 6,535,764 | B2 | 3/2003 | Imran et al. | 2003/0109935 A1 | 6/2003 | Geitz |
| 6,540,789 | B1 | 4/2003 | Silverman et al. | 2003/0120265 A1 | 6/2003 | Deem et al. |
| 6,551,310 | B1 | 4/2003 | Ganz et al. | 2003/0120285 A1 | 6/2003 | Kortenbach |
| 6,554,844 | B2 | 4/2003 | Lee et al. | 2003/0120289 A1 | 6/2003 | McGuckin, Jr. et al. |

| | | |
|---|---|---|
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0225312 A1 | 12/2003 | Suzuki et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0097989 A1 | 5/2004 | Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0194038 A1 | 9/2005 | Brabee et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 1994/18893 A1 | 9/1994 |
| WO | WO 1999/17662 A1 | 4/1999 |
| WO | WO 1999/53827 A1 | 10/1999 |
| WO | WO 2000/32137 A2 | 6/2000 |
| WO | WO 2000/48656 A1 | 8/2000 |
| WO | WO 2000/78227 A1 | 12/2000 |
| WO | WO 2000/78229 A1 | 12/2000 |
| WO | WO 2001/66018 A1 | 9/2001 |
| WO | WO 2001/67964 A2 | 9/2001 |
| WO | WO 2001/85034 A1 | 11/2001 |
| WO | WO 2002/024080 A2 | 3/2002 |
| WO | WO 02/35980 A2 | 5/2002 |
| WO | WO 2002/039880 A2 | 5/2002 |
| WO | WO 2002/071951 A1 | 9/2002 |
| WO | WO 2002/091961 A1 | 11/2002 |
| WO | WO 2002/096327 A2 | 12/2002 |
| WO | WO 2003/007796 A2 | 1/2003 |
| WO | WO 2003/017882 A2 | 3/2003 |
| WO | WO 2003/078721 A2 | 9/2003 |
| WO | WO 2003/086247 A1 | 10/2003 |
| WO | WO 2003/088844 A1 | 10/2003 |
| WO | WO 2003/094785 A1 | 11/2003 |
| WO | WO 2003/099140 A1 | 12/2003 |
| WO | WO 2003/105563 A2 | 12/2003 |
| WO | WO 2003/105671 A2 | 12/2003 |
| WO | WO 2004/009269 A2 | 1/2004 |
| WO | WO 20045/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/053118 A1 | 3/2005 |
| WO | WO 2005/037152 A1 | 4/2005 |
| WO | WO 2005/0548239 A2 | 6/2005 |
| WO | WO 2005/060882 A1 | 7/2005 |
| WO | WO 2006/078781 A1 | 7/2006 |

OTHER PUBLICATIONS

C. Clark, "The Gastric Bubble: Medicine, Magic or Mania?", *SGA J.*, vol. 9, No. 2, 1986, 45-47.

S. L. Edell et al., "Radiographic Evaluation of the Garren Gastric Bubble," *AJR* 145, 1985, pp. 49-50.

D. F. Kirby et al., "Incomplete Small Bowel Obstruction by the Garren-Edwards Gastric Bubble Necessitating Surgical Intervention", *The Am. J. of Gastroenterology*, vol. 82, No. 3, 1987, pp. 251-253.

O. G. Nieben et al., "Intragastric ballon as an artificial bezoar for treatment of obesity", The Lancet, Mar. 27, 1982, pp. 198-199.

T. V. Taylor et al., "Gastric Baloons for Obesity", The Lancet, Mar. 27, 1982, p. 750.

W. L. Percival, MD, "The Balloon Diet": a Noninvasive Treatment for Morbid Obesity. Preliminary Report of 108 Patients, *The Canadian J. of Surgery*, vol. 27, No. 2, 1984, pp. 135-136.

Y. Vandenplas et al., "Intragastric balloons in adolescents with morbid obesity", *European J. of Gastroenterology & Hepatology*, vol. 11, No. 3. pp. 243-245.

B. De Waele, MD et al., "Inragastric Balloons for Preoperative Weight Reduction", *Obesity Surgery*, 10, pp. 58-60.

S. B. Benjamin et al., Abstract, "A Double-Blind Cross Over Study of the Garren-Edwards Anti-Obesity Bubble", *Gastrointestinal Endoscopy*, 1987, Abstract No. 105, vol. 33, No. 2, 1987, p. 168.

S. B. Benjamin, Abstract, "Small Bowel Obstruction and the Garren-Edwards Bubble: Lessons to be Learned?", *Gastrointestinal Endoscopy*, Abstract No. 161, vol. 33, No. 2, 1987, p. 183.

O. W. Cass, Abstract, "Long-Term Follow-Up of Patients with Percutaneous Endoscopic Gastrostomy", *Gastrointestinal Endoscopy*, Abstract No. 162, vol. 33, No. 2, 1987, p. 183.

International Search Report mailed on May 28, 2004, for PCT/US03/27296 filed on Aug. 29, 2003, 5 pgs.

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

Benjamin, S.B., *Small Bowel Obstruction and the Garren-Edwards Bubble, Lessons to Learned?* Abstracts Submitted to A/S/G/E 1987, Division of Gastroenterology, Department of Medicine, Georgetown University Hospital, Washington, D.C.,.

Boyle, Thomas M., M.D., et al., *Small Intestinal Obstruction Secondary to Obturation by a Garren Gastric Bubble,The American Journal of Gastroenterology*, vol. 82, No. 1, pp. 51-53, 1987.

Büchler, M.W., M.D. et al., *A Technique For Gastroplasty As A Substitute For The Esophagus: Fundus Rotation Gastroplasty,Journal Of The American College Of Surgeons*, vol. 182, pp. 241-245, Mar. 1996.

Cass, O.W., et al., *Long-Term Follow - Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D. , et al., *Gastro-Clip®Gastroplasty: A Very Long-Term Complication,Obesity Surgery*, 14, © FD-Communications Inc.. 2004.

Clark, Charlene, R.N., *The Gastric Bubble: Medicine, Magic or Mania?SGA Journal*, vol. 9, No. 2, pp. 45-47, Fall 1986.

Cummings, David E., M.D., et al., *Plasma Ghrelin Levels After Diet-Induced Weight Loss or Gastric Bypass Surgery, New England Journal of Medicine* , vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., *Evolving Concepts of Reflux: The Ups and Downs of the LES,Canadian Journal of Gastroenterology*, vol. 16, No. 5, pp. 327-331, 2002.

De Waele, B., M.D., et al., *Intragastric Balloons for Preoperative Weight Reduction,Obesity Surgery*, vol. 10, pp. 58-60, 2000.

Edell, Steven L., et al., *Radiographic Evaluation of the Garren Gastric Bubble, American Journal of Radiology*, vol. 145, pp. 49-50, Jul. 1985.

Endo Gia *Universal, Single UseStapler and Endo GIA Roticulator*, Brochure, 8 pages, Undated.

Filipi, Charles J. M.D., et al., Transoral, *Flexible Endoscopic Suturing For Treatment Of GERD: A Multicenter Trial, Gastrointestinal Endoscopy*, vol. 53, No. 4, pp. 416-422, 2001.

Gray, Henry, R.R.S., *Anatomy of the Human Body, The Digestive System,* Thirtieth American Edition, pp. 1466-1467 (Undated).

Guidant, Internet, AXIUS™ VACUUM 2 Stabilizer Systems, Internet Website-www.guidant.com/products/axius_vacuum.shtml, 8 pages, visited May 27, 2003.

Hepworth, Clive C. FRCS et al., *Mechanical Endoscopic Methods of Haemostasis For Bleeding Peptic Ulcers: A Review, Bailliere's Clinical Gastroenterology*, vol. 14, No. 3 pp. 467-476, 2000.

Ikeda, Y. et al., *New Suturing Device for Transanal Endoscopic Microsurgery*, Blackwell Science Ltd, p. 1290, 1997.

Johnson & Johnson Gateway[SM] Endopath 3mm, 5mm and 10 mm Diameter Endoscopic Instruments, Internet Website - www.inigateway.com/home.ihtml?loc=USENG&page=viewContent&parentld-0900. . ., 3 pages, visited May 29, 2003.

Kirby, Donald F., *Incomplete Small Bowel Obstruction by the Garren-Edwards Gastric Bubble Necessitating Surgical Intervention, The American Journal of Gastroenterology*, vol. 82, No. 3, pp. 251-253, 1987.

Nieben, Ole Gyring, et al., *Intragastric Balloon as an Artificial Bezoar for Treatment of Obesity, The Lancet*, pp. 198-199, Jan. 23, 1982.

Percival, Walter L., M.D., " *The Balloon Diet": A Noninvasive Treatment for Morbid Obesity.Preliminary Report of 1908 Patients. The Canadian Journal of Surgery*, vol. 27, No. 2, pp. 135-136.

Power Medical Interventions Digital and Wireless Medical Technology, Product Innovation: SurgASSIST™, Internet Website - www/pmi2.com/access_flexibility.asp,6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al. *An Endoscopic Sewing Machine,Gastrointestinal Endoscopy*, vol. 32, No. 1 pp. 36-38 1986.

Villar, Hugo V., M.D., et al., *Mechanisms of Satiety and Gastric Emptying After Gastric Partitioning and Bypass, Surgery*, pp. 229-236, Aug. 1981.

Taylor, T. Vincent, et al., *Gastric Balloons for Obesity, The Lancet*, Abstract, Mar. 27, 1982.

Vandenplas, Y., et al., *Intragastric Balloons in Adolescents With Morbid Obesity, European Journal of Gastroenterology & Hepatology*, vol. 11, No. 3, pp. 243-245, 1999.

Wullstein, C., et al., *Compression Anastomosis(AKA-2) in Colorectal Surgery: Results in 442 Consecutive Patients, British Journal of Surgery 2000* , pp. 1071-1075.

* cited by examiner

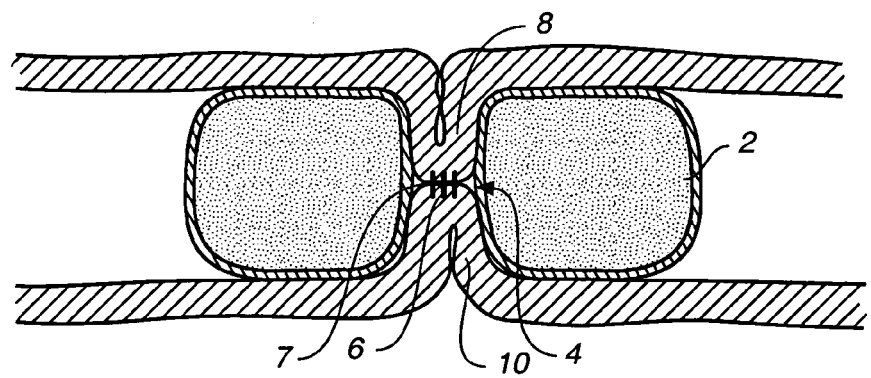
FIG._1
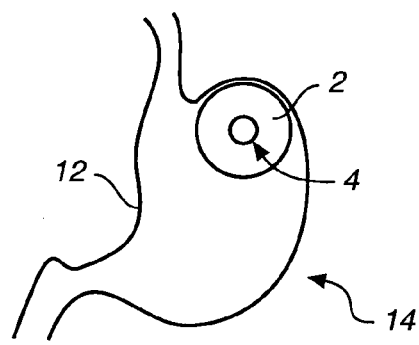
FIG._2
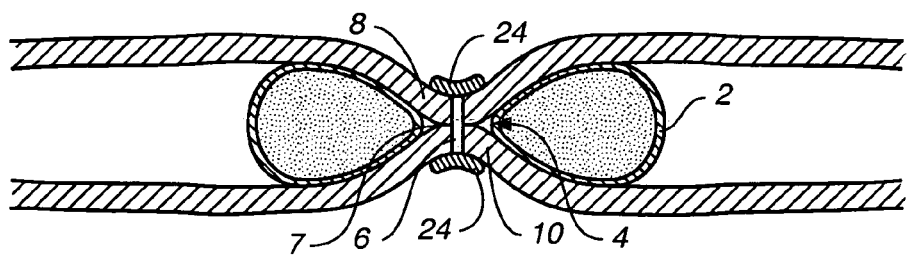
FIG._3

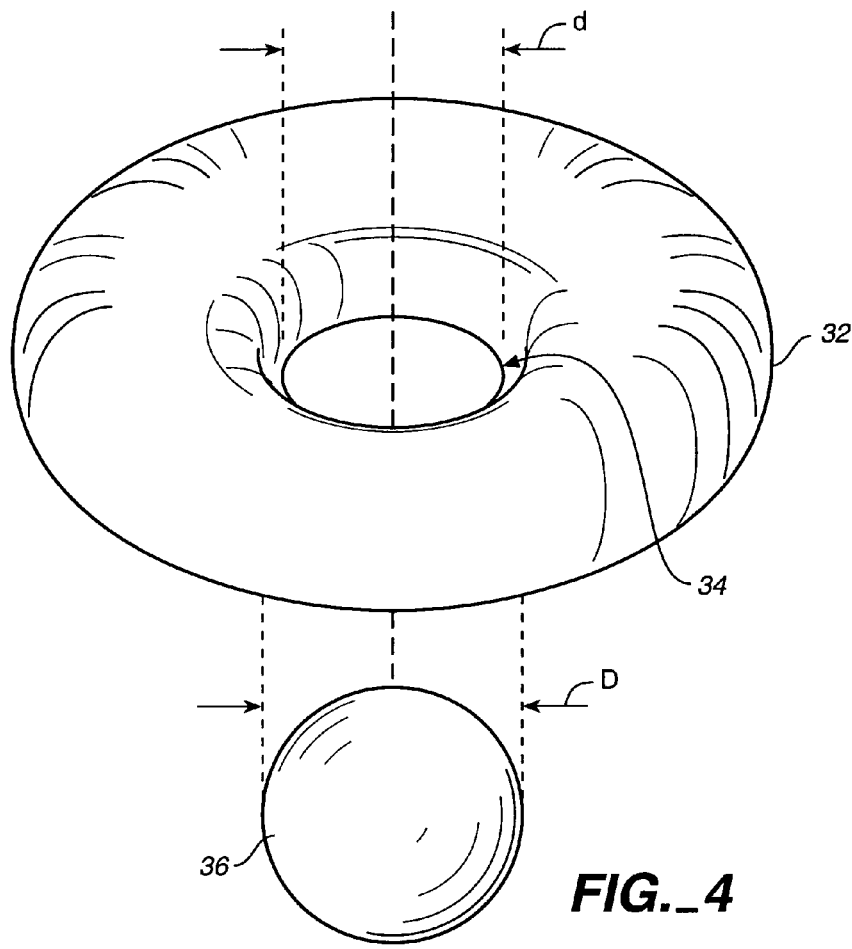
FIG._4
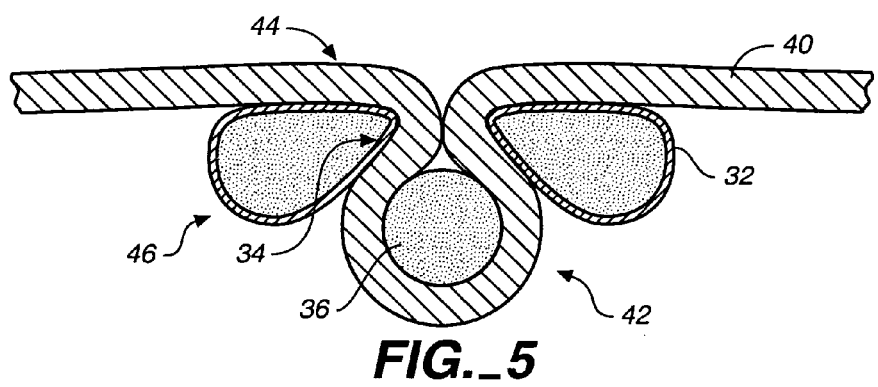
FIG._5

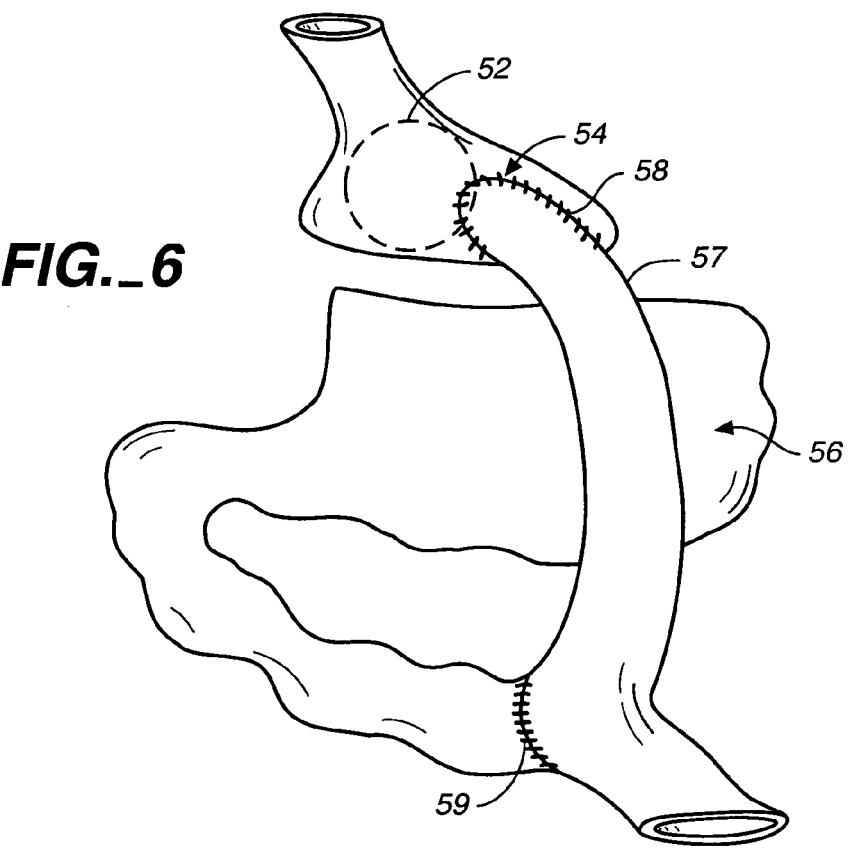
FIG._6
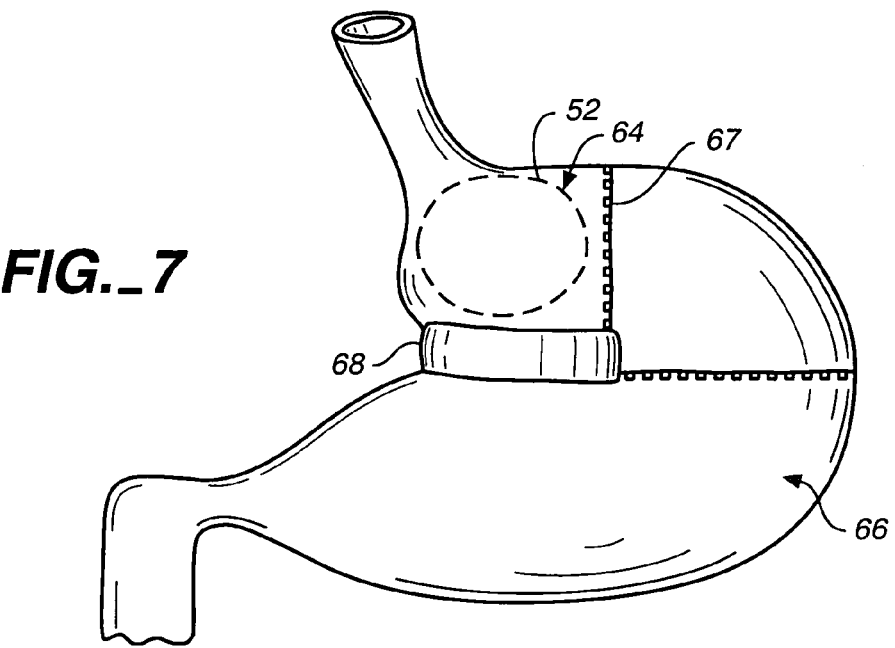
FIG._7

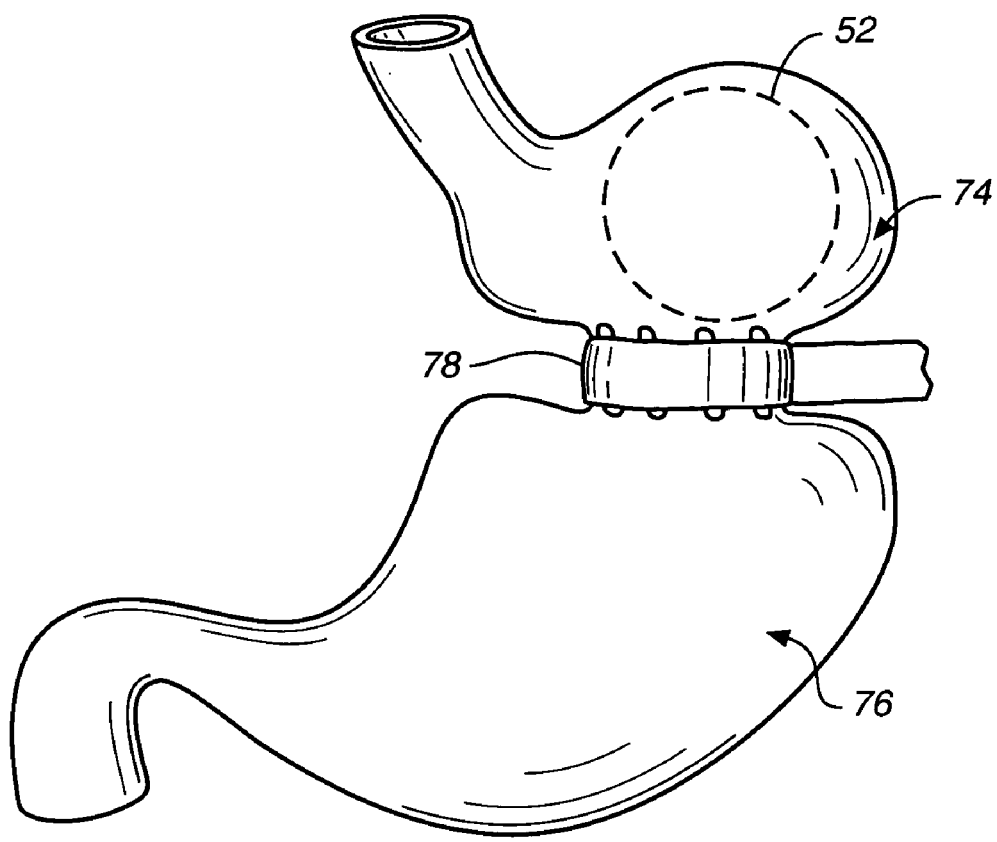
FIG._8

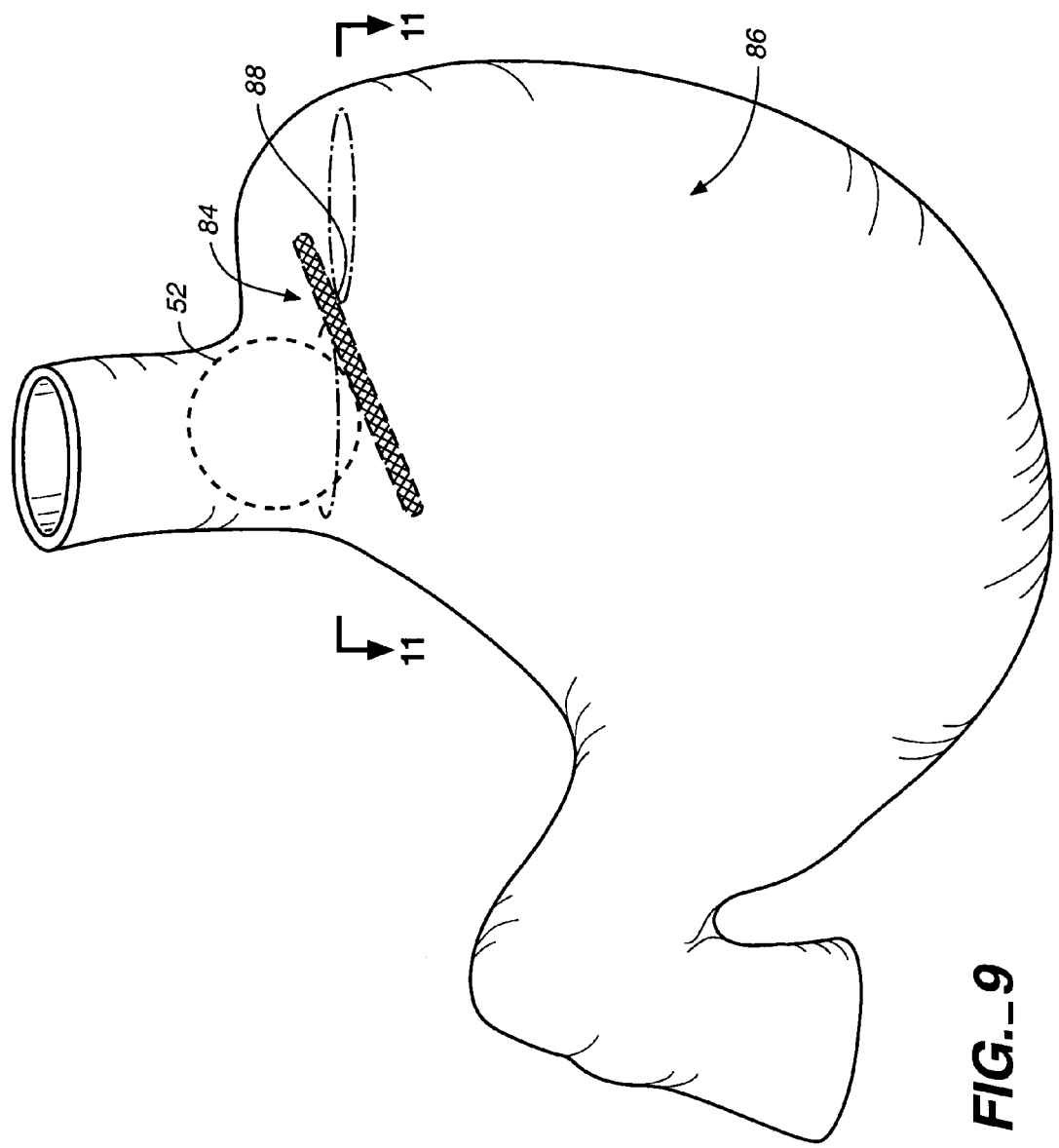
FIG._9

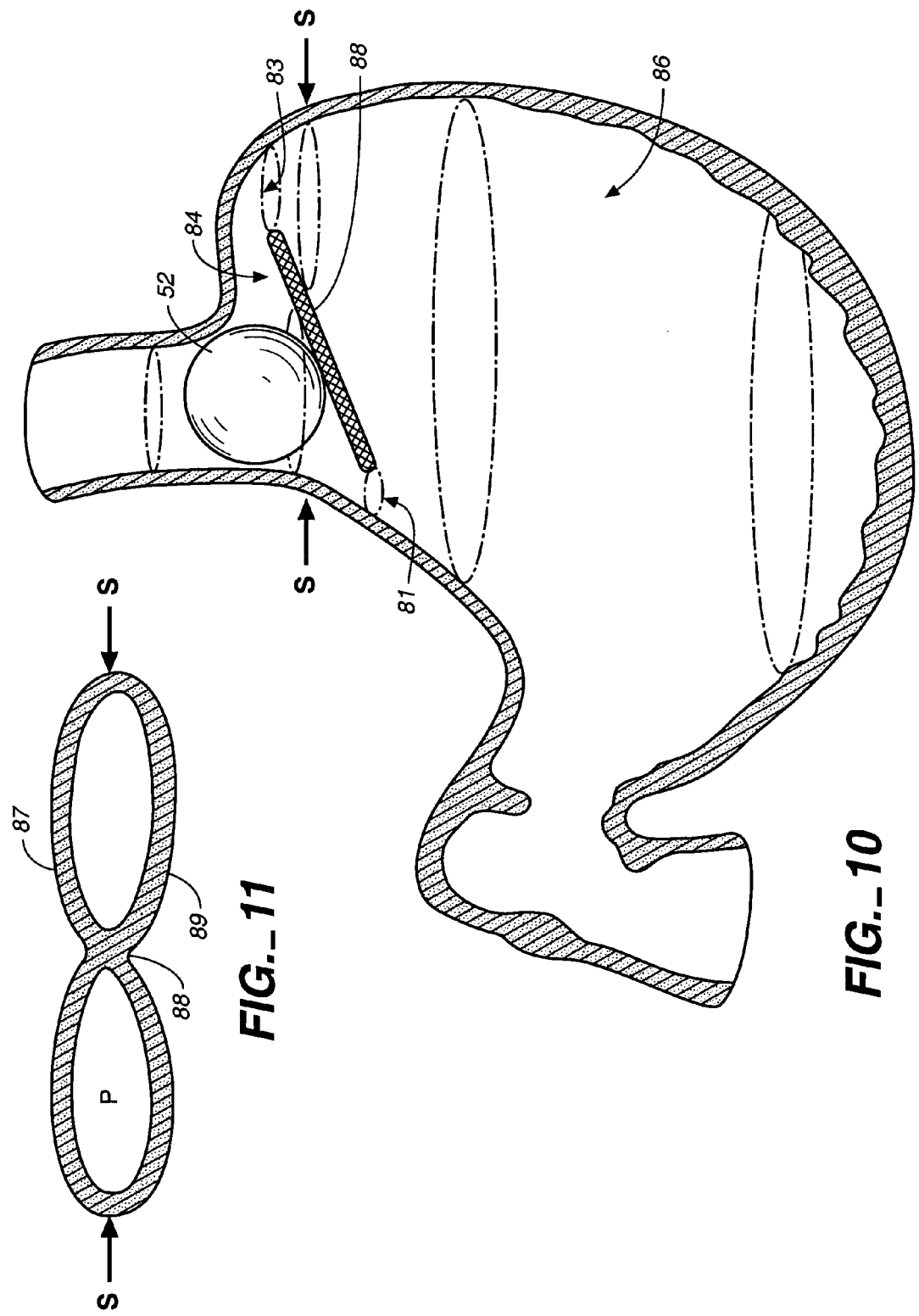
FIG._10
FIG._11

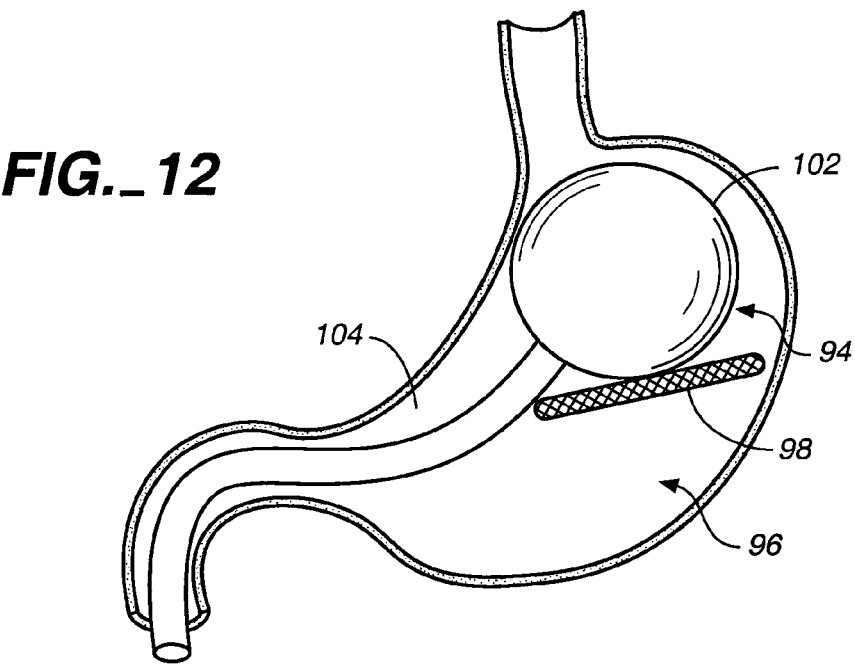
FIG._12
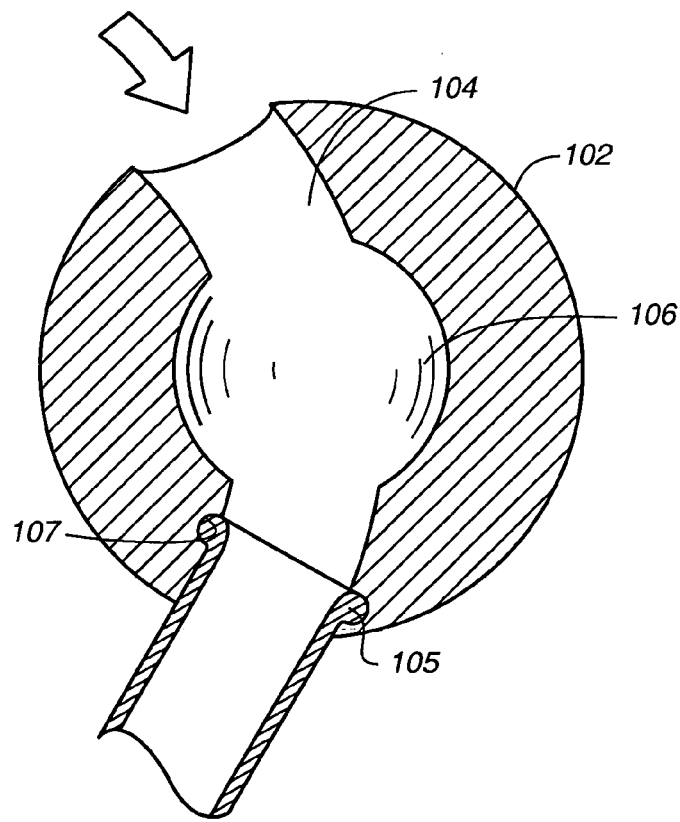
FIG._13

METHODS AND DEVICES FOR MAINTAINING A SPACE OCCUPYING DEVICE IN A RELATIVELY FIXED LOCATION WITHIN A STOMACH

CROSS-REFERENCE TO RELATED APPLICATIONS

The present application is a continuation-in-part and claims the benefit of earlier filed U.S. application Ser. No. 10/232,505, filed on Aug. 30, 2002, now U.S. Pat. No. 6,981,978 which is incorporated herein by reference in its entirety.

BACKGROUND OF THE INVENTION

The present invention relates generally to methods and medical apparatus, more particularly to methods and devices for securing the a space-occupying devices in a patient's stomach through the manipulation of the inner wall of the stomach for purposes of taking up a defined volume in the stomach to provide the patient with a feeling of satiety or fullness. These devices may also be removed once they have served their purpose, e.g., the patient has lost the directed or desired amount of weight.

Currently, in cases of severe obesity, patients may undergo several types of surgery either to tie off or staple portions of the large or small intestine or stomach, and/or to bypass portions of the same to reduce the amount of food desired by the patient, and the amount absorbed by the intestinal track. Procedures such as laparoscopic banding, where a device is used to "tie off" or constrict a portion of the stomach, or the placement of intragastric balloons can also achieve these results.

Endoscopic procedures that have been used to assist weight loss have been primarily focused on the placement of a balloon or other space occupying device in the patient's stomach to fill portions of the stomach and provide the patient with the feeling of fullness, thereby reducing food intake. To accomplish these procedures, an endoscope is utilized to guide the balloon through the patient's mouth and down the esophagus to the stomach. Usually these procedures have allowed placement of the device for 6–12 months, and are coupled with counseling and other types of psychological support.

In the case of laparoscopic banding and other invasive surgical procedures, several complications can arise that make these procedures clinically suboptimal. The surgical interventions require the patient to submit to an intervention under general anesthesia, and can require large incisions and lengthy recovery time. In addition, most of these surgical procedures are irreversible.

Intragastric balloons, on the other hand, provide a minimally invasive approach for treating obesity. Intragastric balloons have been developed and used in patients for over twenty years. Prior to the present invention, various intragastric balloons have been devised for treating obesity. Examples of such intragastric balloons are disclosed in U.S. Pat. No. 4,133,315, issued Jan. 9, 1979 to Berman et al.; U.S. Pat. No. 4,485,805, issued Dec. 4, 1984 to Foster, Jr.; U.S. Pat. No. 4,899,747, issued Feb. 13, 1990 to Garren et al.; U.S. Pat. No. 5,112,310, issued May 12, 1992 to Grobe; and U.S. Pat. No. 6,030,364, issued Feb. 29, 2000 to Durgin et al; each of which is incorporated herein by reference in its entirety. However, many problems are associated with laparoscopic balloons and a significant number of these problems arose due to the fact that the space occupying devices were implanted in such a manner as to remain unattached or free-floating within the stomach. An unsecured balloon could cause abrasion to the wall of the stomach, induce mucosal damage, or stimulate abnormal amounts of acid production. Furthermore, in the event that the balloon deflates due to the caustic nature of stomach acids and other factors, migration of the deflated balloon into the intestine becomes inevitable. The migration of the balloon into the intestine could lead to bowel obstructions and in some case death.

In order to safely and effectively deploy balloons and other space-occupying devices in a patent's stomach to induce weight loss, improved methods and devices for effectively maintaining a space-occupying device in a fixed relationship relative to the patient's stomach are desirable.

BRIEF SUMMARY OF THE INVENTION

The present invention meets these and other needs by providing for improved methods and apparatuses for securing a space-occupying device within a patient's stomach by manipulating the wall of the stomach. Methods and apparatuses of the present invention may also be useful when used in conjunction with existing procedures that result in manipulation of the stomach wall.

Minimally invasive surgical techniques, including but not limited to technique used during a percutaneous endoscopic gastrostomy (PEG), may be combined with methods discussed here for placement of space-occupying devices and at the same time minimize injury to the body. This invention allows placement of space-occupying devices in a patient's stomach in a stable and secured manner.

The space-occupying device may have a fixed volume and may be inserted into the stomach through surgical procedures. However, it is preferable that the space-occupying device is an inflatable or otherwise expandable device, and deliverable or otherwise deployable through the patient's mouth in a transesophageal procedure into the patient's stomach. The expandable space-occupying device may be constructed of a composite material to achieve desirable surface characteristics and may also be visible under x-ray. In addition, the space-occupying device may have surface features, such as a flange, beads, loops, and/or tabs to facilitate manipulation, deflation and/or removal of the device. The volume of the space-occupying device may be adjustable while it is maintained in the deployed condition.

In one aspect of the invention, an expandable device is provided that can be inserted into the stomach of a patient. Its position is maintained within the stomach by manipulating the stomach wall about the device. The expandable device is secured on the wall of the stomach by wrapping a section of the stomach wall around a part of the device. The method may be achieved by securing one region of the stomach wall to another region and at the same time partially encircling a section of the space-occupying device there by holding the space-occupying device to the wall of the stomach. The two regions of the stomach may be secured together with e.g. suture, or other like fasteners. However, more elaborate fastening devices may also be implemented for securing the two regions of the stomach. It is preferable that the two regions of the stomach be brought into physical contact with one another, such that the approximated regions are able to fuse to one another and create a tissue bridge along the length of the fastened tissue. The tissue bridge may be formed of various layers of the stomach and may include scar tissue and other elements of effective wound healing. An advantage of such a method is that integrity of the stomach wall, especially the mucosal layer, remains uncompromised, and exposure of the fastener to the acidic conditions of the stomach is minimized. This is in contrast to other means of fastening a device to the stomach wall where the fastening means present a continuing potential trauma to the stomach wall and wherein such fastening means remain continually exposed to stomach acid.

In a variation of the method described above, the two regions of the stomach used to secure the space-occupying device are opposite each other. A space-occupying device with an opening through its body may be anchored according to this method. The first region of the stomach is brought through the opening on the device and into contact with the second region. A suture or other fastening device may be used to secure the two regions together. The space-occupying device implemented in this method may be e.g. toroidal or any other shape suitable for placement inside the stomach, provided the device contains an opening through the center of the device that provides a passageway from one side of the device to the other.

In another variation, multiple stomach regions may be approximated to secure a space-occupying device. For example, three regions may be used, e.g. region one and two are secured onto region three or are otherwise brought into approximation with each other. In an alternative variation, after the first set of surface areas are brought into approximation with each other, additional surface areas on the inner wall of the stomach may be brought into approximation of each other. For example, the space-occupying device may be secured by two sets of approximated surface areas that secure the device at two different locations on the device.

In another aspect, the invention provides a space-occupying system or kit that consists of two portions, a sphere and a toroid. The sphere when properly deployed acts as a "locking member" and in connection with the toroid itself is able to maintain the toroid against the inner wall of the stomach. Procedures and methods for implementing such a system in the stomach are also within the contemplation of this invention. In one variation, a deflated toroidal shaped balloon is first deployed inside the patient's stomach, and a region of the stomach wall is then forced through the center opening of the toroidal balloon. A sphere is then deployed from the external side of the stomach, passed through the center opening of the toroidal balloon and inserted within the same region of stomach tissue. The sphere has a diameter that is greater than that of the toroidal balloon center opening when the toroidal balloon itself is inflated. Thus, upon inflation of the toroidal balloon the sphere and associated region of stomach tissue is trapped against the toroidal balloon, and cannot pass back through the center opening of the balloon, thus anchoring the toroid on the inner surface of the stomach wall. In the above procedure, it may also be possible to concurrently pass the regions of stomach wall through the toroid along with the spherical locking member. Preferably, the regions of the stomach that are trapped within the opening of the toroidal balloon are held in physical contact with one another, such that the regions are able to fuse to one another and create a tissue bridge along the length of the approximated regions. Such a tissue bridge has the advantages previously described.

In other variation of the dual-member-interlocking system for securing a space-occupying device on the wall of the stomach, the space-occupying device may be of various shapes suitable for placement inside a patient's stomach, and include an opening passing through the body of the space-occupying device. The corresponding locking member may be expandable or of a fixed shape. The space-occupying device in its deflated state may allow the corresponding member to pass through its opening. The space-occupying device is placed inside the patient's stomach and the corresponding locking member is place inside the patient's body, and outside the stomach. Through e.g. vacuum pull, physical pushing/pulling, or a combination of both, the locking member is put through the opening of the space-occupying device. If necessary, the locking member may be expanded at this stage. The space-occupying device is then inflated holding the locking member in its place.

In yet another aspect of the invention, methods are provided wherein a pouch is created within the stomach that is able to receive and retain a space-occupying device within the pouch. Such pouches can be created according to known methods currently used to reduce stomach volume, including gastric bypasses, such as the Roux-En-Y gastric bypass, vertical banded gastroplasty (VBG), or laproscopic banding. Methods of creating a pouch capable of receiving and retaining a space occupying device also include those methods of plicating the stomach described in U.S. application Ser. No. 09/871,297, filed May 30, 2001, which is commonly owned and incorporated herein by reference. Such plication methods include methods where transorally advanced tools are used to form a pouch or partition in the stomach by the approximation and fixation of folds of the stomach wall from inside the stomach. In one such exemplary procedure, folds in the posterior and anterior walls of the stomach are created using a tissue acquisition device inserted into the stomach transorally, and then the two folds of tissue are fixed together thereby reducing stomach volume. The tissue folds may be fixed together in a variety of configurations. Space-occupying devices can be deployed in the created pouches either initially to aid in the efficacy of the procedures, or post-procedure as a means, e.g., of enhancing the efficacy of such procedures.

In a further aspect of the invention, methods are provided wherein a pouch is created within the stomach that is able to receive and retain a space-occupying device within the pouch, and wherein the device is further designed to include a passageway extending through the device and a cavity within the device in communication with the passageway, the cavity further having a predefined volume. The device is introduced into the pouch with the passageway in alignment with the esophagus so as to receive and pass food. The cavity thus creates, in essence, a smaller artificial pouch within the originally created stomach pouch. This allows for convenient manipulation to optimize weight loss in a patient without the need of further interventional procedures, by simply adjusting the cavity volume of the deployed device. This can be done, for example, by initially starting with a larger volume cavity device, monitoring the patient's progress, and transorally exchanging the device for one of sequentially smaller cavity volumes, until the desired weight loss parameters are achieved. Alternatively, the device can be provided with a cavity volume that is adjustable. In particular, inflation or filling ports are provided on the device that can be accessed transorally, and the cavity volume can be adjusted by inflation or deflation. In a further variation, the passageway and cavity of the device are relatively rigid as compared to the rest of the device, allowing for a slow, constant release of food unaffected by the peristaltic action of the stomach. In a further variation, the device includes a sleeve extending from the passageway for the passage of food directly through the pylorus and into the duodenum.

BRIEF DESCRIPTION OF THE DRAWINGS

In the accompanying drawings, reference characters refer to the same parts through out the different views. The drawings are intended for illustrating some of the principles of the invention and are not intended to limit the description in any way. Furthermore, the drawings are not necessarily to scale, emphasis instead being placed upon illustrating the depicted principles in a clear manner.

FIG. 1 shows one variation of the method to anchor a space-occupying device in the stomach according to the invention. Two regions of the stomach that are located across from each other in the stomach are brought together at the opening in the center of the space-occupying device and fastened to each other.

FIG. 2 illustrates an example of applying the method described in FIG. 1 to maintain a toroidal space-occupying device at the upper portion of a patient's stomach.

FIG. 3 shows another embodiment of the inventive method wherein a space-occupying device is secured in the stomach by a fastener that secures two separate regions of stomach wall together.

FIG. 4 illustrates an embodiment of a space-occupying device locking system according to the invention. In this variation, the system includes an inflatable toroidal space-occupying device and an inflatable spherical locking member.

FIG. 5 is a cross-sectional view of a space-occupying device locking system according to FIG. 4 deployed on the wall of a patient's stomach. The extragastric balloon is surrounded by a region of stomach wall that interacts with the toroidal intragastric balloon and prevents the two balloons from moving.

FIG. 6 illustrates another aspect of the invention wherein a space-occupying device is retained within a pouch created in the stomach through manipulation of the stomach wall. In the variation depicted, the stomach pouch has been created by performing a Roux-En-Y gastroplasty.

FIG. 7 illustrates a variation of the method shown in FIG. 6, where the pouch has been created by a vertical band gastroplasty.

FIG. 8 illustrates a variation of the method shown in FIG. 6, where the pouch has been created by laproscopic banding.

FIG. 9 illustrates a variation of the method shown in FIG. 6, where the pouch has been created by plication of the stomach.

FIG. 10 is a cross-sectional view of the stomach and space-occupying device depicted in FIG. 9, showing the created pouch, stomach plication line and the retained space-occupying device.

FIG. 11 is a sectional view of the stomach depicted in FIG. 9 taken along the plane designated by lines 11—11 showing the plication of the stomach.

FIG. 12 illustrates yet another aspect of the invention wherein a space-occupying device is retained within a pouch created in the stomach, the space-occupying device having a passageway and extending sleeve configured to pass food from the patient's esophagus to the pylorus.

FIG. 13 illustrates a cross-sectional view the deployed space-occupying device of FIG. 12 with parts broken away, showing a cavity within the device in communication with the passageway.

DETAILED DESCRIPTION OF THE INVENTION

The present invention is focused on methods and devices for maintaining a space-occupying device in a relatively fixed position within a patient's stomach. Various methods and devices for deployment of a space-occupying device in a human stomach that are well know to one skilled in the art may be incorporated with the present methods and devices in executing the procedure for deploying a space-occupying device inside a patient's stomach and securing its location within the stomach. International Application No. PCT/US01/43868 (International Publication No. WO 02/35980 A2) describes various tools, devices and methods for deployment of expandable devices inside a patient's body cavity. It is incorporated herein by reference in its entirety.

Referring to FIG. 1, one variation of the method according to the present invention of maintaining a space-occupying device 2 in a fixed relationship to a patient's stomach is illustrated in detail. The space-occupying device 2 is adapted for occupying a defined amount of space within the stomach to provide the patient with a feeling of fullness. The space-occupying device 2 is delivered into the patient's stomach in the deflated state through a transesophageal procedure. The space-occupying device 2 is then inflated inside the patient's stomach. With the assistance of an endoscope, catheters and other surgical tools well known to one skilled in the art, a surgeon may place the space-occupying device on the inner wall of the stomach. As shown in FIG. 1, the surgeon brings together two regions 8, 10 of the stomach within an opening 4 on the space-occupying device and secures the two regions 8, 10 to each other. The two regions 8, 10 of the stomach to be brought together may be located opposite one another. Although it is preferable that the two regions 8, 10 be directly opposite each other, this not a necessary requirement in the application of this method and one skilled in the art will appreciate that a variety of different region locations can be used to achieve the desired result.

In the example illustrated in FIG. 1, the toroidal space-occupying device 2 is secured in the stomach by fastening two regions 8, 10 of the stomach that are located on the opposite side of the stomach within the center passage way of the toroidal device. This may be achieved e.g. by first passing an elongated surgical instrument through the opening on the toroid and then securing an area on the inner wall of the stomach. This first area of the stomach is then pulled through the toroidal opening. The first area of the stomach is then brought in contact with a second area. At least one fastener 6 is then deployed to connect the two areas 8, 10 of the stomach. FIG. 2 illustrates a toroidal space-occupying device 2 secured at the upper portion of a patient's stomach 14 with the method described above. The posterior and anterior regions of the stomach that corresponds to the opening on the toroid are brought together in the opening and fastened to each other. Alternatively, a space-occupying device 2 may also be placed in other locations within the stomach. For example, the space-occupying device 2 may be positioned more towards the center of the stomach.

It is preferable, that the two regions 8, 10 of the stomach come in contact with each other. As illustrated in FIG. 3, the two regions 8, 10 of the stomach may be brought into approximation and fastened to each other with a fastener 6.

Furthermore, various fasteners 6 may be used to secure the two areas 8, 10 of the stomach. It is preferable that the space-occupying device deployed in this manner has an opening 4 allowing the stomach tissue to pass through it. However, the space-occupying device 2 may be of various shapes one skilled in the arts considers suitable for deployment inside a patient's stomach.

Although it is preferable that the two regions 8, 10 of the stomach tissue that are brought together within the opening of the space-occupying device be translated approximately the same distance, it is also within the contemplation of this invention that one region of tissue may be translated more than the other, resulting in the meeting point 7 or the gap 26 being shifted away from the center of the space occupying device toward one side or the other.

Alternatively, the space-occupying device 2 may be deflated or only partially inflated when it is being secured with the wall of the stomach. Once the space-occupying device is secured at the desired position, it is then fully inflated.

The two regions 8, 10 of the stomach may be fastened to each other with the assistance of endoscopic instruments through the esophagus. The fastener 6 may only partially penetrate the stomach wall without penetrating the outer wall of the stomach.

Alternatively, sutures may also be used to secure the space-occupying device that extend through the external wall of the stomach. For example, the space-occupying device is positioned in the stomach, a needle with a suture is inserted from the outside of the stomach through the wall of the stomach into the stomach. The surgeon then passes the needle through the opening on the space-occupying device and exits the stomach through the wall on the opposite side. The surgeon then brings the needle along with the connected suture back into the stomach at approximately the same region and passing the opening again, and exits the stomach at a location near the first entry point. The two ends of the sutured are then secure to each other. As pressure is applied due to the tightening of the suture, the two regions 8, 10 of the stomach collapse toward each other and meet inside the opening within the space-occupying device.

In another variation, a laproscopic instrument can be used to deliver a fastener through the stomach from extragastric space. The fastener is inserted into the abdomen and then through the anterior of the stomach. The fastener is then pushed through the opening of the space-occupying device and through the stomach wall on the posterior side. An anchor is then deployed, followed by application of pressure to force the two side of the stomach to collapse toward each other. A second anchor is then deployed on the opposite side of the stomach. The laproscopic instrument is then withdrawn from the body of the patient leaving the fastener to securing the two region of the stomach. The result is similar to the situation shown in FIG. 3, where anchors 24 are located outside the stomach, which have a large surface area relative to the entry and exit points of the fastener 6, and allow distribution of pressure from the fastener 6 over a larger area of the stomach tissue thus minimizing potential damage to the tissue due to tearing or abrasion of the tissue.

In another variation, the stomach wall is wrapped around the space-occupying device to maintain its position within the stomach. The surgeon may secure one region of the stomach wall and places it over the space-occupying device. The surgeon then secures a second region of the stomach wall and places it over the space-occupying device. A fastener is then used to secure the two regions of the stomach over the space-occupying device. The fastener may be a suture, a surgical staple, a surgical clip, an implantable loop, or other devices commonly used in surgery for securing two sections of tissues together. As discussed earlier, the two regions of the stomach do not have to come in contact with each other. It is sufficient that they are in approximation of each other.

Although it is preferable that the two regions of the stomach tissue wrapping over the space-occupying device be approximately the same amount, it is also within the contemplation of this invention that one region of tissue may be more than the other, resulting in the meeting point or the gap be shifted away from the center of the space occupying device toward one side or the other.

Alternatively, the space-occupying device may be deflated or only partially inflated when it is being anchored to the wall of the stomach. After the space-occupying device is secured at the desired location then it is fully inflated.

In the above method, other minimal invasive surgical techniques that are well know to one skilled in the art may also be incorporated to assist the positioning of the space-occupying device with the inner wall of the stomach. The surgeon may make incisions on the abdomen and introduce catheters and other laproscopic instruments into the stomach through the extra-gastric space. For example, the surgeon may insert an elongated laproscopic fastener instrument through the abdomen into the stomach. The fastener is then used to secure one region of the stomach wall, place it over an intragastric balloon, then position this first region of the stomach wall over a second region of the stomach wall, and then deploy a fastener to fasten the two regions of the stomach together.

Alternatively, the surgeon may introduce a needle connected to a suture into the abdomen of the patient and then penetrate the wall of the stomach with the needle at a first region and bring a section of the suture into the stomach. The suture is brought over the space-occupying device and exits the stomach at a second region. The needle then penetrates the stomach around the second region and enters the stomach again. The needle and a section of the suture are then brought over the space-occupying device and exit the stomach adjacent the first entry point. The suture is tightened and as the result forcing the two regions of stomach tissue to collapse inward and wrapping around the space occupying device.

The inflatable space-occupying device may be fabricated from medical grade rubber or synthetic rubber-like material, one criteria being that such material be impervious so that the insert is capable of holding a charge of air or other fluid. Moreover, the material may be soft and flexible having significant dynamic strength to resist over-inflation. In one variation of the design, the finished product will inflate to the manufactured shape and not further. Polyester base thermoplastic polyurethane film is one material that may be used to achieve such functionality. In an alternative design, the inflatable space-occupying device may be produced of flexible synthetic materials such as polyethylene, polypropylene, PVC, PVCD, PET, teflon, polyolefin or any other appropriate type of materials well known to one skilled in the art.

When the intragastric balloon is inflated, it may be desirable to carefully control the inflation pressure so that when the balloon is deployed the internal pressure is higher than average intragastric pressure during digestion to maintain shape, but less than maximal pressure generated by the stomach contractions, to minimize mucosal damage.

The space-occupying device may be of various shapes that one skilled in the art would consider suitable for placement inside the stomach of a patient. For example, in one variation, the space-occupying device may have an elongated bar shaped body with distal ends having larger diameters than the mid-section of the device. This narrow mid-section allows easier wrapping of stomach tissue over the device and the expanded ends prevent the device from shifting its position after it is secured with the stomach wall. Radio opaque markers may be incorporated on the space-occupying device to assist physician in monitoring the position and status of the space-occupying device while it is inside a patient's body. Alternatively, it may be desirable to coat the space-occupying device with radio-opaque materials or other substances that may enhance the detection of the space-occupying device by electronic monitors, e.g. x-ray monitor or ultrasound monitor, while the space-occupying device is in the patient's stomach.

In another variation, the space-occupying device is secured with the wall of the stomach at two or more locations. For example, a toroidal shaped space-occupying device can be secured against the wall of the stomach at two separated positions on the toroid.

FIG. 4 shows yet another embodiment of the invention having a space-occupying device 32 with an opening 34, in this case a toroidal intragastric balloon, and a locking member 36, in this case spherical extragastric balloon. The toroid 32 has a center opening with a diameter "d" when it is fully inflated. The sphere 36 has a diameter "D" when it is fully inflated. D is larger then d. Thus, when both the toroid 32 and the sphere 36 are inflated the sphere 36 cannot pass through the opening 34 of the toroid.

FIG. 5 illustrates the toroidal intragastric balloon 32 and the spherical extragastric balloon 36 being deployed on the wall of stomach 40. A deflated toroidal (or doughnut shaped) intragastric balloon 32 is inserted into the stomach through the esophagus. A region 42 of the stomach wall is pulled into a fold or bag inside the stomach using e.g. a vacuum acquisition tool. The deflated toroidal intragastric balloon 32 is positioned around the fold (or uvula). The spherical extragastric balloon 36 is then placed either laproscopically or gastroscopically (using transgastric deployment) inside the fold in the extragastric space 44, and then inflated. The intragastric balloon 32 is then inflated and the two balloons become locked together across the gastric wall 40. Because the diameter of the inflated sphere 36 is larger than the diameter of the opening of the inflated toroid 32, there is a mechanical interference between the two balloons that prevents the two balloons from moving relative to one another or the stomach.

The balloons may be constructed of various materials that one skilled in the art would consider suitable for fabrication of a balloon for implantation inside a human body. For example, the intragastric and extragastric balloons may be fabricated from medical grade rubber or synthetic polymeric materials. Flexible synthetic materials such as polyurethane, polyethylene, polypropylene, PVC, PVCD, PET, teflon, their mixtures and blocks or random copolymers may also be used.

Radio opaque makers may be incorporated in the space-occupying device 32 and/or the locking member 36. The surface of the space-occupying device and/or the locking member may be coated with radio-opaque materials to enhance detection of the device while it is positioned in a patient's stomach.

In an alternative design, the extragastric balloon 36 may be substituted with a viscous, curable bolus of a material such as collagen or other biocompatible polymer. The locking member may also be a solid component such as delrin, silicon or titanium alloy ball. Other polymers or metal alloys may also be used to construct the locking member.

Although it is preferable that the intragastric balloon 32 be toroidal or doughnut shape, the intragastric balloon 32 may also have other shapes suitable for implantation inside a patient's stomach. In an alternative design, the space-occupying device 32 is a non-inflatable object with a relatively constant volume that is insert into a patient's stomach through the esophagus or with surgical procedures. After the insertion of the fixed-shape space-occupying device, an expandable locking member 36 is used to anchor the space-occupying device on the wall of the stomach as described above.

Referring now to FIGS. 6–11, the present invention also contemplates methods of retaining space-occupying devices that rely on the creation of retaining pouches within the stomach through manipulation of the stomach or stomach wall. In current obesity treatments, the creation of such pouches is the desired result of a variety of gastroplasty procedures. The purpose of most of these procedures is to create a smaller, upper gastric pouch within the stomach, through manipulation of the stomach walls. As the smaller, upper gastric pouch expands or stretches upon intake of food, a feeling of early fullness is triggered in the patient, which ideally results in reduced overall caloric intake by the patient. According to methods of the present invention, these pouches can also serve to receive and retain space occupying devices of the appropriate corresponding configurations. Due to the physical constraints of the pouches themselves, these space occupying devices are maintained in place relative to the stomach as a whole and restricted from migrating out of the pouch. The provision of a space occupying device within a formed gastric pouch further lessens the amount of food intake that will trigger a feeling of fullness in the patient. The space occupying devices can be deployed at the time of the gastroplasty procedure itself to enhance the efficacy of the gastroplasty. In other scenarios, such as where a formed gastric pouch has become stretched out over time or has otherwise failed to provide the desired clinical effect, a space occupying device can be inserted at such later time to increase or enhance the desired effect.

FIG. 6 in particular shows an upper, gastric pouch 54 formed from a gastric bypass procedure commonly known as a Roux-en-Y gastric bypass (RYGB) procedure. In this procedure, the stomach is completely divided into two unequal portions, the smaller upper, gastric pouch 54 and a larger, lower gastric pouch 56, using e.g. an automatic stapling device with the raw surface being reinforced with additional sutures. The upper pouch typically measures less than about 1 ounce or 20 cc, while the lower larger pouch remains generally intact and continues to secrete stomach juices flowing through the intestinal tract. Segment 57 of the small intestine (located just distal of the duodenum or proximal of the jejunum) is then brought from the lower abdomen and joined with the upper pouch 54 to form an end-to-end anastomosis 58 created through an opening or stoma of approximately one-half inch in upper pouch 54. This segment of the small intestine is called the "Roux loop" and carries food from the upper pouch to the remainder of the intestines, where the food is digested. The remaining lower pouch 56 and the attached segment of duodenum are then reconnected to form another anastomotic connection 59 to the Roux loop at a location approximately 50–150 cm (1.6–4.9 ft) from the stoma, typically using a stapling instrument. At this connection, the digestive juices from the bypassed stomach, pancreas, and liver enter the jejunum or ileum to aid in the digesting of food. As with other similar gastroplasty procedures, due to the small size of the upper pouch, patients are forced to eat at a slower rate and are satiated much more quickly, thereby reducing the caloric intake.

Space-occupying device 52 is placed and maintained within upper gastric pouch 54 and further lessens the volume of pouch 54. Space-occupying device 52 as depicted is spherical in shape but other configurations may used that generally conform to the shape of the formed pouch. The space-occupying device can be formed of materials and deployed according to ways previously described herein.

FIG. 7 shows an upper, gastric pouch 64 formed from a vertical banded gastroplasty (VBG) procedure. In this type of a procedure, upper gastric pouch 64 can be typically formed using a vertical staple line 67, with band 68 applied to prevent dilation of the outlet from upper pouch 64 into the remaining portion of the stomach which forms lower pouch 66. Again, space occupying device 52 is placed and retained within upper pouch 64. Alternative methods of performing vertical banded gastroplasty may also be used, including those methods described in U.S. Pat. No. 5,549,621, incorporated herein by reference.

FIG. 8 shows an upper gastric pouch 74 formed by a laproscopic banding procedure. In this type of a procedure, laproscopic methods and tools are used to insert a banding device 78 that constricts the stomach wall, creating upper and lower gastric pouchs 74 and 76, respectively. Space occupying device 52 is deployed and retained within upper pouch 74. Variations on such laproscopic banding methods may also be used, including those methods described in U.S. Pat. No. 5,345,949, incorporated herein by reference.

FIGS. 9–11 show an upper gastric pouch 84 created by methods of plication of the stomach wall. Preferred methods include those described in U.S. application Ser. No. 09/871,297, filed May 30, 2001, which is commonly owned and incorporated herein by reference. Such described methods include plication methods wherein transorally advanced tools are used to form a pouch or partition in the stomach by the approximation and fixation of folds of stomach. Referring to FIGS. 9–11, folds in the posterior wall 87 and anterior wall 89 of the stomach may be created using a tissue acquisition device inserted into the stomach transorally, and then the two folds of tissue may be fixed together using staples or other fastening means to create a linear segment or line of plicated tissue 88. The plicated tissue runs at an angle relative to the esophogeal lumen, resulting in the formation of upper gastric pouch 84. Space occupying device 52 is received and retained with gastric pouch 84. As can be-seen, the plication of the anterior and posterior walls does not extend across the entirety of the stomach, thereby leaving small openings 81 and 83 at either end of the plication for food to pass into the lower gastric pouch 86.

The above methods of retaining space-occupying devices in created pouches can also be adapted for situations where it is difficult to perform a gastroplasty procedure, either by transoral stapling or other methods previously described, at a more optimal location such as in close proximity to the cardiac notch (or GE junction) of the stomach. In such situations, it may be advantageous to perform the stapling at a more accessible location, i.e., lower in the stomach from the cardiac notch. In this scenario, the resultant pouch may have a volume on the order of 150–200 ccs, as compared to more desirable volumes for optimal weight loss conditions of from 20–50 ccs. However, in such a situation, whether the larger pouch was created either purposefully or inadvertently, a larger space-occupying device commensurate in size with the larger pouch can be selected and deployed according to the methods described herein.

FIGS. 12–13 illustrate one such application, where staple line 98 has been placed at a lower position relative to the cardiac notch, thereby creating upper and lower pouches 94 and 96, respectively. Upper pouch 94 has a larger relative volume as compared to upper pouches depicted in FIGS. 6–11. A space-occupying device, here depicted as intragastric balloon 102, is selected to have shape and commensurate volume proportionate to that of upper pouch.

Referring now to FIG. 13, it can be seen that intragastric balloon 102 is further provided with a passageway 104 extending through the balloon and a cavity 106 in communication with the passageway. The passageway is oriented such that it is aligned with the patient's esophagus. In this manner, food can be received and travel through the passageway. In the interior of the device, passageway 104 opens up into cavity 106 which has a defined volume. Cavity 106, in essence, defines an artificial pouch, that is smaller in volume than the originally created upper stomach pouch 94.

This system can be readily and conveniently manipulated by a physician to adjust a patient's weight-loss treatment program without the need for additional surgery. For example, a treating physician can initially place a space-occupying device, such as intragastric balloon 102, that has a relatively larger cavity volume. As the patient's weight loss progress is monitored, the physician can as warranted, transorally exchange the device with one having sequentially smaller cavity volumes, until the desired weight loss conditions, rate of loss, or other parameters, are achieved. In this manner, the degree and pace of weight loss can be finely tuned, without need for additional invasive procedures.

Alternatively, intragastric balloon 102 can be constructed such that the volume of cavity 106 is adjustable. For example, the device can be inflatable and further provided with an inflation or filling port or ports (not shown) that are accessible to a transorally-advanced endoscope. Inflation media can then be introduced into or released from the balloon to alter the size of the cavity. Such adjustments could also affect the overall volume of the balloon which can increase stretching of the gastric pouch itself, further affecting weight loss.

In a further variation, passageway 104 and cavity 106 can be made to be somewhat rigid relative to the remaining components of the balloon. In such a variation, the exterior portions of the balloon will flex and expand or contract to a much greater degree than the passageway. As a result, the dimensions of the passageway and cavity remain fairly constant, and food that enters and fills the cavity will empty at a constant rate and not be impacted by stretching and contraction of the stomach. In other words, the normal peristaltic effect of the stomach on food contained in the passageway or cavity will be diminished. This may slow the overall release of food from the device and further contribute to a more desired and controllable weight loss pattern in the patient.

As also shown in FIG. 12, intragastric balloon 102 further includes a sleeve that extends from passageway 104. This sleeve can be positioned as shown to extend through pyloris and pyloric valve of the stomach and into the duodenum of the small intestine. As shown in FIG. 13, the sleeve can be attached to the balloon by the provision of rim 105 which is securable to corresponding recess 107 in passageway 104, although one of ordinary skill in the art will recognize other known methods of attachment. The provision of the sleeve allows food to pass directly into the small intestine and, depending on the overall length of the sleeve, can operate to avoid absorption of nutrients by the duodenum altogether.

Depending on the clinical situation, the inclusion of the bypass sleeve may be of further advantage.

This invention has been described and specific examples of the invention have been portrayed. The use of those specifics is not intended to limit the invention in anyway. Additionally, to the extent there are variations of the invention, which are within the spirit of the disclosure or equivalent to the inventions found in the claims, it is our intent that this patent will cover those variations as well.

We claim the following:

1. A method of maintaining a space-occupying device in a fixed relationship relative to a patient's stomach wall comprising the steps of
   providing a space-occupying device;
   introducing said space-occupying device into the patient's stomach to a location adjacent an inner wall of the stomach;
   bringing a first surface area of the inner wall of the stomach into approximation with a second surface area of the inner wall of the stomach; and
   securing said first surface area to said second surface area such that the space-occupying device is retained at a fixed location relative to the stomach.

2. The method of claim 1 wherein said approximating step further results in a portion of the inner wall surrounding a portion of the space-occupying device.

3. The method of claim 1 wherein the provided space-occupying device is an intragastric balloon.

4. The method of claim 3 wherein the introducing step further comprises the step of inflating the space-occupying device.

5. The method of claim 1 wherein the securing step comprises suturing said first surface area to said second surface area.

6. The method of claim 5 wherein the securing step comprises suturing said first surface area to said second surface area from inside the stomach without penetrating the outer wall of the stomach.

7. The method of claim 1 wherein the approximating step comprises approximating a first and a second surface area located opposite one another.

8. The method of claim 1 further comprising the steps of
   bringing additional surface areas on the inner wall of the stomach into approximation with one another; and
   securing said additional surfaces to one another.

9. The method of claim 1 wherein the securing step further comprises the use of a fastener to secure said first surface to said second surface.

10. The method of claim 1 wherein the securing step further comprises the step of introducing a fastener tool to deploy a fastener for securing said first surface to said second surface.

11. The method of claim 1 wherein the providing step comprises providing a toroid-shape space-occupying device.

12. The method of claim 11 wherein the first and the second surfaces are opposite each other.

13. The method of claim 12 wherein the approximation step further comprises the step of bring said first surface area through a center opening of said toroid-shape space-occupying device.

14. A method of anchoring a space-occupying device on a patient's stomach wall comprising the step of,
   providing an inflatable space-occupying device having a passageway there through;
   introducing said inflatable space-occupying device into the stomach to a location adjacent to a first region of the stomach wall;
   placing an spherical member adjacent the first region on the outside of said stomach;
   forcing said spherical member and said first region of the stomach wall through the passage way of the space-occupying device while the space-occupying device is in a deflated state; and
   inflating said space-occupying device and trapping said spherical member, thereby securing said space-occupying device to the patients stomach wall.

15. The method of claim 14 wherein the providing step comprises providing a toroidal space-occupying device having a passageway there through.

16. The method of claim 14 wherein:
   the providing step comprises providing an inflatable toroidal intragastric balloon;
   the placing step comprises placing an inflatable spherical extragastric balloon adjacent the first region on the outside of said stomach; and
   the forcing step further comprises applying suction to said first region of the stomach wall to form a fold, inserting said deflated extragastic balloon into the fold, and inflating said spherical extragastric balloon.

17. A method of assisting weight loss in a patient comprising the steps of:
   a) creating a pouch within the patient's stomach;
   b) selecting a first space-occupying device adapted for placement and retention within the pouch, the first space-occupying device having a passageway extending through the device, and a cavity within the device and in communication with the passageway, the cavity having a first defined volume;
   c) introducing the space-occupying device into the created pouch such that the passageway is oriented in alignment with the patient's esophagus;
   d) monitoring the patient's weight loss, and, if warranted
   e) replacing the first space-occupying device with a second space-occupying device adapted for placement and retention within the pouch, the second space-occupying having a passageway extending through the device, and a cavity within the device and in communication with the passageway, the cavity having a second defined volume, such that the passageway is oriented in alignment with the patient's
   esophagus, the second defined volume of the second space-occupying device being different than the first defined volume of the first space-occupying device.

18. A method of assisting weight loss in a patient comprising the steps of,
   a) creating a pouch within the patient's stomach;
   b) selecting a space-occupying device adapted for placement and retention within the pouch, the space-occupying device having a passageway extending through the device, and a cavity within the device and in communication with the passageway, the cavity having an adjustable volume;
   c) introducing the space-occupying device into the created pouch such that the passageway is oriented in alignment with the patient's esophagus;
   d) monitoring the patient's weight loss, and, if warranted
   e) adjusting the cavity volume of the space-occupying device.

* * * * *

UNITED STATES PATENT AND TRADEMARK OFFICE
CERTIFICATE OF CORRECTION

PATENT NO. : 7,214,233 B2
APPLICATION NO. : 10/366818
DATED : May 8, 2007
INVENTOR(S) : James Gannoe et al.

It is certified that error appears in the above-identified patent and that said Letters Patent is hereby corrected as shown below:

<u>Title page,</u>
(*) Notice, delete "This patent is subject to a terminal disclaimer."
Item (57), ABSTRACT, line 12, delete "capable holding" and insert --capable of holding--.

<u>Page 4</u>, FOREIGN PATENT DOCUMENTS, delete "WO 2005/053118" and insert --WO 2005/023118--.
OTHER PUBLICATIONS, delete "O.G. Nieben et al., "Intragastric ballon as an artificial bezoar for treatment of obesity" and insert --"Intragastric balloon as an artificial bezoar for treatment of obesity"--.
Delete "T.V. Taylor, et al., " "Gastric Baloons for Obesity" " and insert --"Gastric Balloons for Obesity"--.

<u>Page 5</u>, OTHER PUBLICATIONS, delete "*A Double-Blind Cross Over Study of the Garren-Edwards anti-Obesity Bubblem*" and insert --*A Double-Blind Cross Over Study of the Garren-Edwards anti-Obesity Bubble*--.

<u>Column 1,</u>
Line 19, delete "the a space-occupying" and insert --space-occupying--.

<u>Column 4,</u>
Line 4, delete "place" and insert --placed--.

<u>Column 5,</u>
Line 64, delete "view the" and insert --view of the--.

<u>Column 6,</u>
Line 35, delete "this not" and insert --this is not--.

<u>Column 7,</u>
Line 34, delete "sutured are then secure" and insert --suture are then secured--.
Line 46, delete "two side of the stomach" and insert --two sides of the stomach--.
Line 50, delete "securing the two region" and insert --secure the two regions--.

<u>Column 8,</u>
Line 9, delete "be" and insert --being--.
Line 17, delete "know" and insert --known--.
Line 39, delete "as the result forcing" and insert --the result forces--.
Line 40, delete "wrapping" and insert --wrap--.

UNITED STATES PATENT AND TRADEMARK OFFICE
CERTIFICATE OF CORRECTION

PATENT NO. : 7,214,233 B2
APPLICATION NO. : 10/366818
DATED : May 8, 2007
INVENTOR(S) : James Gannoe et al.

It is certified that error appears in the above-identified patent and that said Letters Patent is hereby corrected as shown below:

Column 9,
Lines 5 and 56, delete "Radio opaque" and insert --Radio-opaque--.
Line 25, delete "then" and insert --than--.

Column 10,
Line 2, delete "doughnut shape" and insert --doughnut shaped--.
Line 6, delete "insert" and insert --inserted--.

Column 13,
Line 5, delete "anyway" and insert --any way--.
Line 58, delete "bring" and insert --bringing--.

Column 14,
Line 41, delete "occupying having" and insert --occupying device having--.

Signed and Sealed this

Thirty-first Day of July, 2007

JON W. DUDAS
*Director of the United States Patent and Trademark Office*